United States Patent [19]

Taschner

[11] Patent Number: 5,433,930
[45] Date of Patent: Jul. 18, 1995

[54] SCREEN BASKET FOR STERILIZATING CONTAINERS

[75] Inventor: Wolfgang Taschner, Tuttlingen, Germany

[73] Assignee: AESCULAP AG, Tuttlingen, Germany

[21] Appl. No.: 671,762
[22] PCT Filed: Sep. 23, 1989
[86] PCT No.: PCT/EP89/01109
   § 371 Date: Mar. 22, 1991
   § 102(e) Date: Mar. 22, 1991
[51] Int. Cl.⁶ .................. A61L 2/00; A61L 2/26
[52] U.S. Cl. .................... 422/300; 24/657;
   24/671; 24/672; 24/673; 206/370; 206/438;
   206/480; 422/292
[58] Field of Search .......... 422/292, 297, 300;
   248/221.4; 24/665, 657, 671, 672, 673; 206/363,
   369, 370, 438, 480

[56] References Cited

U.S. PATENT DOCUMENTS

| | | | |
|---|---|---|---|
| 1,265,869 | 5/1918 | Arkin | 24/657 |
| 1,443,277 | 1/1923 | Robinson | 24/672 |
| 2,316,145 | 4/1943 | Futrell | 422/300 |
| 2,929,177 | 3/1960 | Kosswig | 422/300 X |
| 4,262,799 | 4/1981 | Perrett | 422/300 X |
| 4,643,303 | 2/1987 | Arp et al. | 422/300 X |
| 4,928,917 | 5/1990 | Wolf | 422/300 X |

FOREIGN PATENT DOCUMENTS

| | | | |
|---|---|---|---|
| 2713094 | 10/1978 | Germany . | |
| 2929227 | 10/1980 | Germany | 422/300 |
| 8702485 | 5/1987 | Germany . | |

Primary Examiner—Robert J. Warden
Assistant Examiner—Krisanne M. Thorton
Attorney, Agent, or Firm—Barry R. Lipsitz

[57] ABSTRACT

A screen basket is provided for sterilizing containers, having a bottom with openings therein. Holding elements are fixed on the bottom, each having an extension which extends through at least one opening of the bottom. A releasable fixing member provided for each extension is placed on the underside of the bottom, to facilitate the installation and removal of the holding elements. Each extension has at least one recess on a side surface thereof. The fixing members carry a detent element which engages the recess in the corresponding extension. The detent element is held on the fixing member for removal from the recess by elastic deformation.

16 Claims, 3 Drawing Sheets

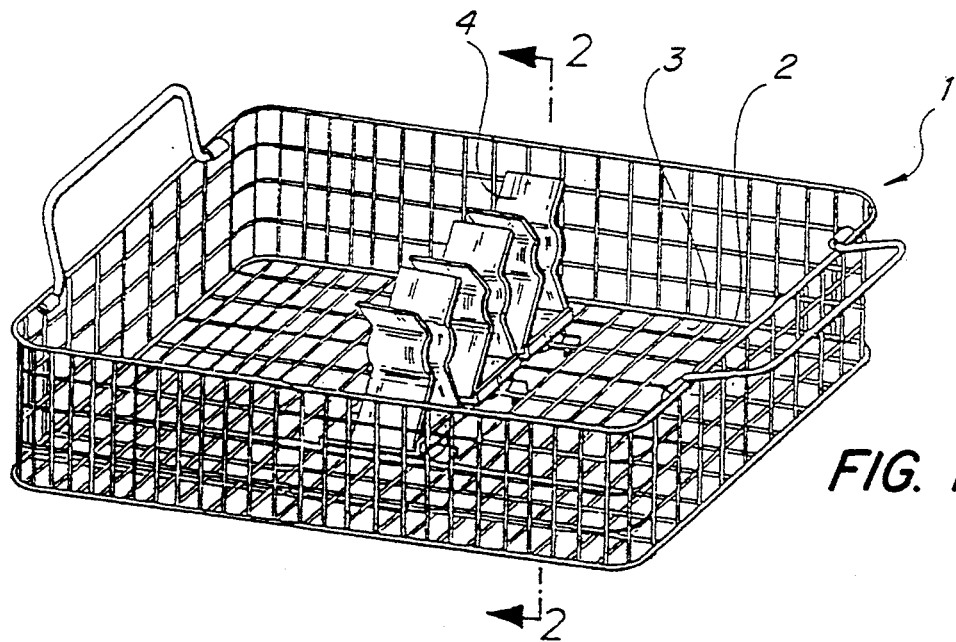
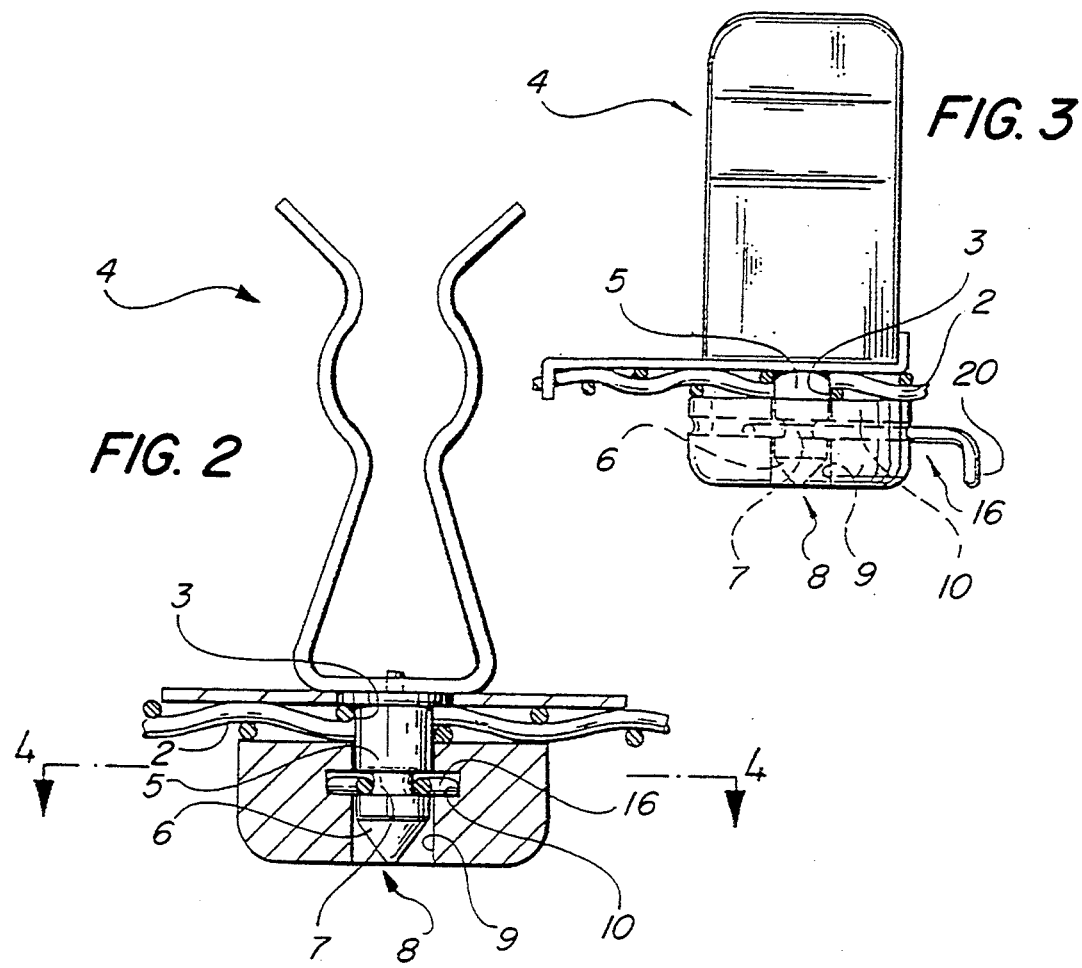

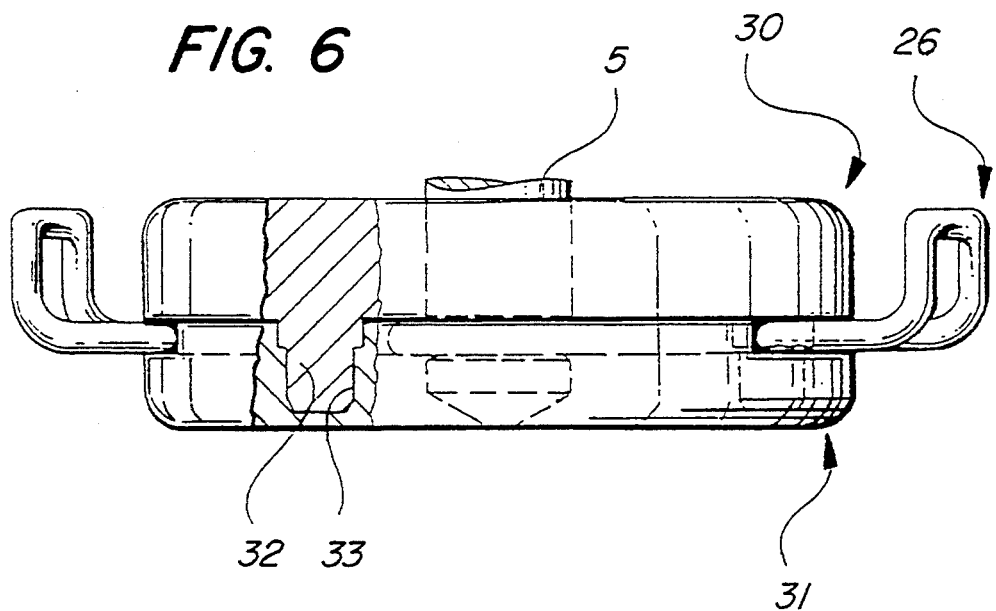
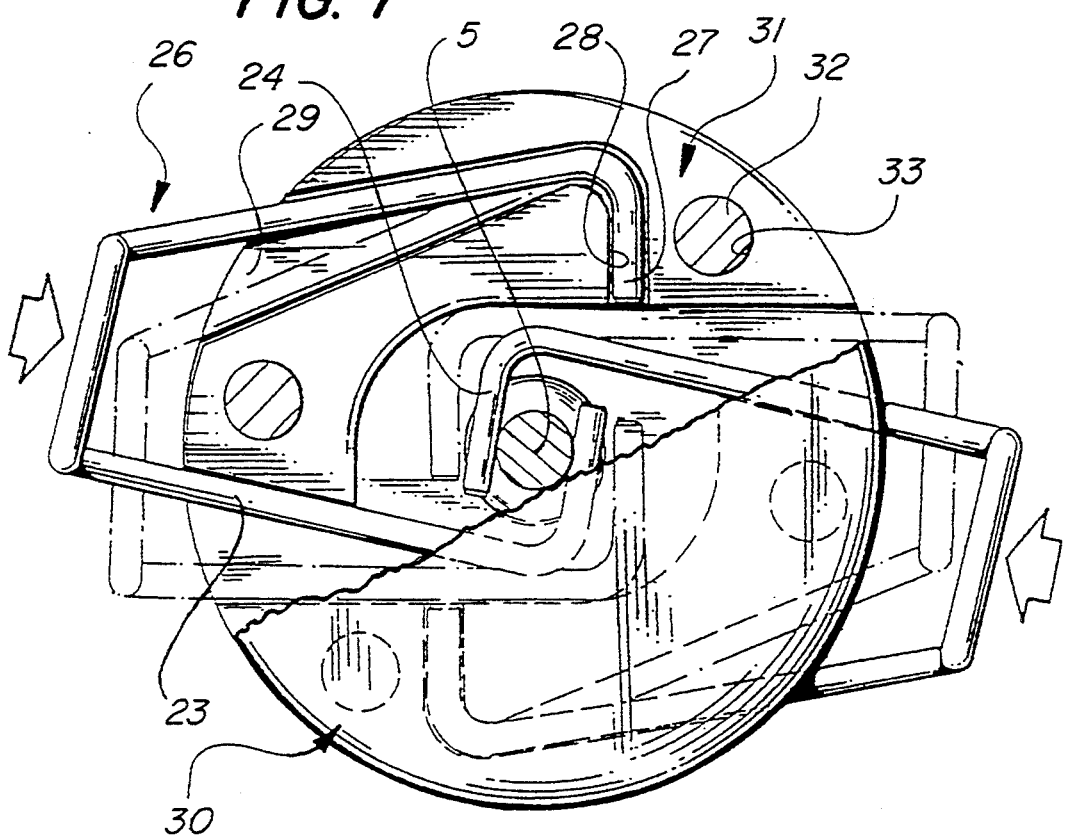

SCREEN BASKET FOR STERILIZATING CONTAINERS

The invention relates to a screen basket for sterilizing containers comprising a bottom with openings therein and holding elements fixed on the bottom and having an extension which extends through at least one opening of the bottom and onto which a releasable fixing member surrounding the extension is placed on the underside of the bottom.

Such a screen basket with fixing members designed in the fashion of a nut and screwable onto extensions carrying an external thread is known from German patent 2 713 094. Such screen baskets have worked exceedingly well as it is possible to attach holding elements in this way to any points on the basket.

Proceeding from this prior art, the object underlying the subject matter of the application is to simplify the fixing of the holding elements at various points on the bottom of the screen basket and, in particular, the putting-on and removing of the fixing members on the extensions.

This object is accomplished in accordance with the invention in a screen basket of the kind described at the beginning in that the extension has at least one recess on its side surfaces, in that the fixing member carries a detent element which engages the recess at the side and is held on the fixing member for removal from the recess by elastic deformation, in that the detent element comprises two parallel resilient detent arms, the mutual spacing of which is less than the outer diameter of the extension, in that the two detent arms are mounted in the fixing member for displacement parallel to their longitudinal direction, and in that contact surfaces extending away from one another are provided for the detent arms in the path of displacement of the ends of the detent arms.

This enables placing of the fixing members in a simple way on the extension, with the elastic detent element engaging a recess at the side of an extension and thus being fixed on the extension. The fixing member is released by elastic deformation of the detent element which is then moved out of the recess at the side and releases the fixing member again. Thus, the fixing member is fixed by simply putting it on and removed again by deformation of the detent element, which constitutes a clear simplification in comparison with the screwing-on and off of known fixing members. It is particularly advantageous for the recess on the extension to be a circumferential groove and for the detent element to engage the annular groove on opposite sides of the extension.

Provision may be made for the extension to carry a tip which rests against the detent element and pushes it elastically to the side when the fixing member is pushed onto the extension. Hence when the fixing member is put on, no additional deformation of the detent element is required by the operator as this takes place automatically with the putting-on of the fixing member.

In a preferred embodiment provision is made for the detent element to comprise two parallel resilient detent arms, the mutual spacing of which is less than the outer diameter of the extension, for the two detent arms to be mounted in the fixing member for displacement parallel to the longitudinal direction and for contact surfaces extending away from one another to be provided for the detent arms in the path of displacement of the ends of the detent arms. The non-deformed detent element thus engages with its detent arms the recesses in the extension and fixes the extension with respect to the fixing member. To release it, the detent arms are displaced parallel to themselves and then come to rest with their end against the contact surfaces extending away from one another which thereby bend open the two detent arms until the detent arms are elastically bent out of the recesses of the extension. It is then readily possible to remove the fixing member from the extension.

The contact surfaces may advantageously be formed by a wedge of the fixing member which is oriented towards an insert opening for the extension.

It is particularly expedient for the fixing member to comprise a shaft which extends transversely to an insert opening for the extension and is open at the side and into which the detent element which protrudes laterally from the shaft is pushed, for the two ends of the detent arms to be bent aside and, when the detent arms are not deformed, to engage a widening at the sides of the shaft, for the detent arms to be joined together by a crosspiece at their end which protudes from the shaft, and for the shaft to be so wide that the detent arms can be elastically bent apart until their mutual spacing corresponds at least to the outer diameter of the extension. The detent element is undetachably held in the fixing member by the ends of the detent arms which are bent aside, and the side walls of the shaft guide the detent element so it can be moved in a precisely defined manner in the shaft when pressure is applied to the crosspiece connecting the two detent arms.

Herein, it is, furthermore, expedient for the bent ends of the detent arms to be so short that they lie completely within the interior of the shaft when the detent arms are bent together. It is thereby possible, merely by bending the detent arms together, to insert the detent element into the fixing member and to remove it from the latter again. In spite of this, it remains undetachably held in the fixing member after insertion.

The detent arms may be crank shaped, with their spacing in the region near the crosspiece being greater than in the region penetrating the insert opening. The detent element is thereby also secured against being pushed sideways in the shaft by the detent arms, i.e., by the spacing of the detent arms being only slightly less than the width of the shaft.

If the detent arms are bent perpendicularly at their end near the crosspiece which protrudes from the shaft, the fixing member can be of very flat design and yet the detent element can be easily pushed into the fixing member for the purpose of releasing it.

It is particularly advantageous for the detent element to be integrally made of spring wire.

The object is also accomplished in accordance with the invention in a screen basket of the kind described at the beginning in that the extension has at least one recess on its side surfaces, in that the fixing member carries a detent element which engages the recess at the side and is held on the fixing member for removal from the recess by elastic deformation, in that the detent element engages with the bent end of a detent arm an insert opening for the extension in the fixing member, the detent arm being mounted in the fixing member for displacement transversely to the insert opening, emerging from the fixing member and being resiliently pushable into the fixing member.

This detent arm can be fixed by a spiral spring attached at one end to the fixing member and at its other end to the detent arm in a position in which the bent end of the detent arm dips into the insert opening. By pressing on the detent arm against the action of the spiral spring, the bent end of the detent arm is pushed out of the insert opening, thereby enabling removal of the fixing member from the extension.

Here, too, it is expedient for detent arm and spiral spring to be integrally made of spring wire.

Provision may be made for the one end of the spiral spring to be bent aside and to engage a retaining recess in the fixing member. In this case, it is advantageous for the detent arm to comprise at the transition to the spiral spring a pressure section which extends transversely to the detent arm and facilitates elastic insertion of the detent arm.

Such an embodiment is particularly advantageous when two detent arms of identical design with bent ends are arranged diametrically opposite in the fixing member. Only when both detent arms are elastically pressed into the fixing member is removal of the fixing member from the extension possible. This prevents the fixing member from sliding off the extension unintentionally if one detent arm is inadvertently pushed elastically into the fixing member, as might be the case when one is busy with the screen basket and the pressure section of the detent arm is pushed against a firm object.

In the preferred embodiment, provision may be made for the fixing member to be divided into two halves in the plane of the detent arm and the spiral spring, for the one end of the spiral spring and the adjoining part of the spiral spring to be inserted in a groove in one half of the fixing member which is open towards the plane dividing the two halves, and for the two halves to be joined together after insertion of the spiral spring in the groove. In such an embodiment, the spiral spring is not inserted into the fixing member through the shaft at the side but is placed in the open groove of one half of the fixing member and subsequently the two halves of the fixing member are joined together so the spiral spring is thereby undetachably held in the fixing member.

In this case, it is advantageous for the two halves to be aligned relative to each other by pins and corresponding holes in which the pins engage.

The two halves may consist of plastic and be lastingly joined together by ultrasonic welding.

The following description of preferred embodiments serves in conjunction with the drawings to explain the invention in further detail.

BRIEF DESCRIPTION OF THE DRAWINGS

FIG. 1 a perspective view of a screen basket with holders inserted in its bottom;

FIG. 2 a sectional view along line 2—2 in FIG. 1 with a first preferred embodiment of a fixing member pushed onto the extension of the holder;

FIG. 3 a side view of the holder of FIG. 2;

FIG. 6 a side view of a modified embodiment of a fixing member comprised of two halves; and FIG. 7 a plan view of the fixing member of FIG. 6 wherein the top half is partly broken away.

FIG. 1 a screen basket is illustrated as used as insert in sterilizing containers for sterilizing surgical instruments and the like. The screen-like bottom 2 comprises a plurality of openings 3. Holders 4 for instruments and the like comprise at their bottom end a pin-shaped extension 5 which can be pushed through any opening 3 and then protrudes, downwards from the bottom 2. The extension 5 carries a conical tip 6 and adjoining the latter a circumferential annular groove 7 which forms a recess with respect to the outer circumference of the pin-shaped extension 5.

A disc-shaped fixing member 8 having a continuous insert opening 9 for receiving the pin-shaped extension 5 is placed from below on the pin-shaped extension to fix a holder 4.

Figure 4:
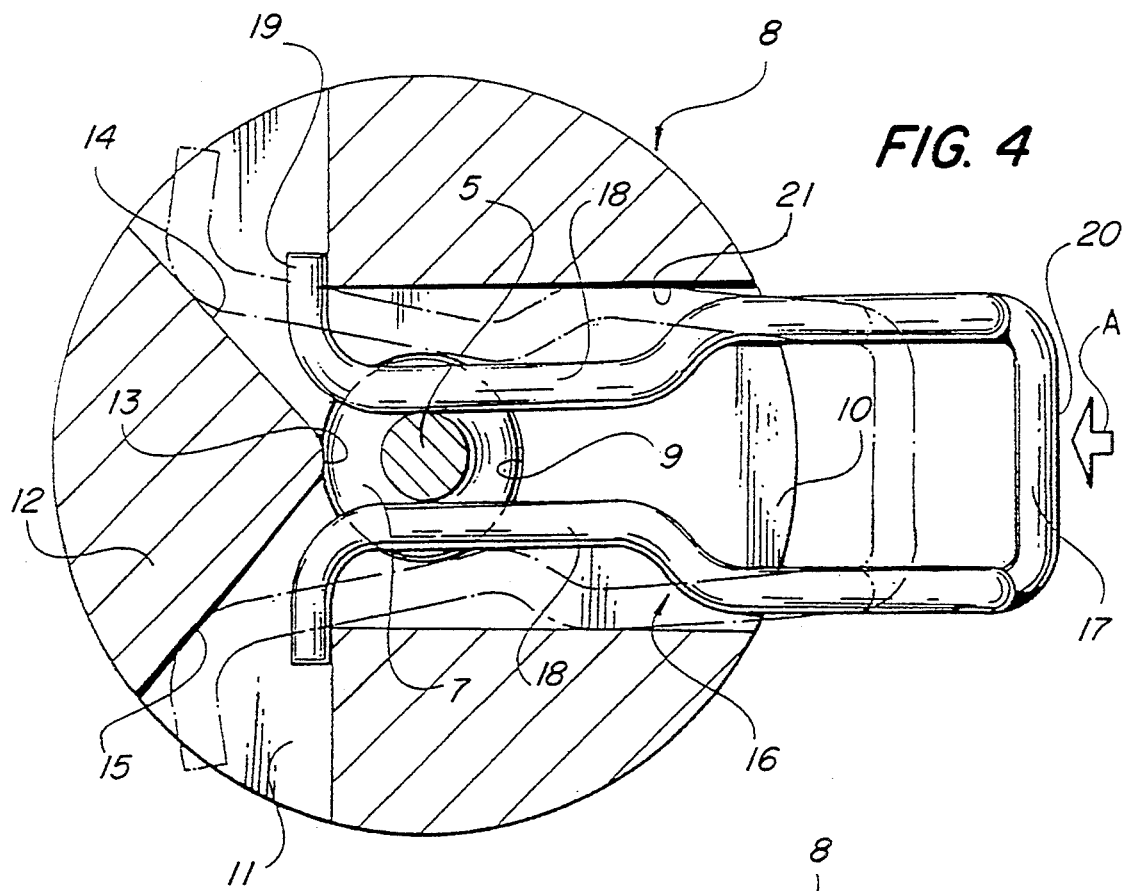
FIG. 4 a sectional view along line 4—4 in FIG. 2.

In the first embodiment illustrated in FIGS. 2 to 4, the disc-shaped fixing member 8 comprises a shaft 10 extending parallel to the bottom 2 and hence perpendicular to the insert opening 9. The shaft 10 is open on one side thereof towards the circumference of the disc-shaped fixing member 8. The shaft extends from the open end beyond the insert opening 9 and then widens in the shape of a step, with the widening 11 extending as far as the circumference of the fixing member 8 (FIG. 4). At the side opposite the open end of the shaft 10, the widening 11 is delimited by a wedge 12 which is oriented with a tip 13 towards the insert opening 9 and comprises two contact surfaces 14 and 15 extending substantially perpendicular to each other (FIG. 4).

The shaft 10 is arranged in the fixing member 8 at such a height that it is aligned with the annular groove 7 in the extension 5 when the holder 4 is pressed firmly against the bottom 2 and the fixing member 8 pushed onto the extension 5 rests with surface-to-surface contact against the underside of the bottom 2, as illustrated in FIG. 2.

A substantially U-shaped detent element 16 which is integrally bent from spring wire and comprises resilient detent arms 18 extending parallel to each other and connected to one another by a crosspiece 17 is inserted into the shaft 10. The detent arms 18 are mutually spaced from one another in their region near the crosspiece at a distance which is only slightly less than the width of the shaft 10, but they are crank shaped approximately at their center and so in the front region the detent arms 18 are spaced at a distance from one another which is less than the diameter of the insert opening 9 and the outer diameter of the pin-shaped extension 5. The detent arms 18, therefore, dip in this front region into the insert opening 9 (FIG. 4). The free ends 19 of the detent arms are bent outwards at a right angle and engage the widening 11, i.e., when the detent element 16 is not deformed, the spacing of the bent ends 19 from one another is greater than the width of the shaft 10. However, the length of the bent ends 19 is selected such that when the detent arms 18 are bent together, the spacing of the bent ends 19 is less than the width of the shaft 10 so it is possible to push the detent element into the shaft or out of it again when the detent arms are bent together.

The detent arms 18 are bent perpendicularly downwards in their region near the crosspiece (FIG. 3), thereby forming an approximately U-shaped pressure section 20 protruding perpendicularly downwards and extending perpendicularly to the plane of the shaft 10.

The U-shaped detent element is inserted into the shaft in the manner described herein by bending the two detent arms together until the two bent ends 19 engage the widening 11. After relaxation of the detent element, the two bent ends 19 secure the detent element against being pulled out of the shaft 10, the detent arms 18 lie in the rear region exhibiting a greater spacing from one another almost against the inside wall of the shaft 10 so sideward tilting of the detent element in the shaft is avoided, i.e., the detent element is guided in the longitudinal direction in the shaft.

When the fixing member is pushed onto the pin-shaped extension, the two detent arms dipping into the insert opening 9 are elastically bent apart by the tip 6 of the extension 5 so the extension 5 can be pushed into the insert opening 9, with the two detent arms 18 resting elastically against the outer circumference of the ex-extension 5 until the extension is completely pushed into the fixing member 8. The detent arms 18 then snap elastically into the annular groove 7 and thereby prevent withdrawal of the fixing member 8 from the extension 5.

To release the fixing member from the extension again, it is sufficient to press the detent element radially into the fixing member 8 in the direction of arrow A in FIG. 4.

The bent ends 19 of the detent arms 18 thereby come to rest against the contact surface 14 and 15 of the wedge 12 and, when the detent element is pushed in further, bend the detent arms in the manner illustrated in dot-and-dash lines in FIG. 4 so far apart that the spacing of the detent arms corresponds to the outer diameter of the extension 5, i.e., the detent arms are completely pushed out of the insert opening 9. In this position, the fixing member can be readily removed from the extension 5.

Figure 5:
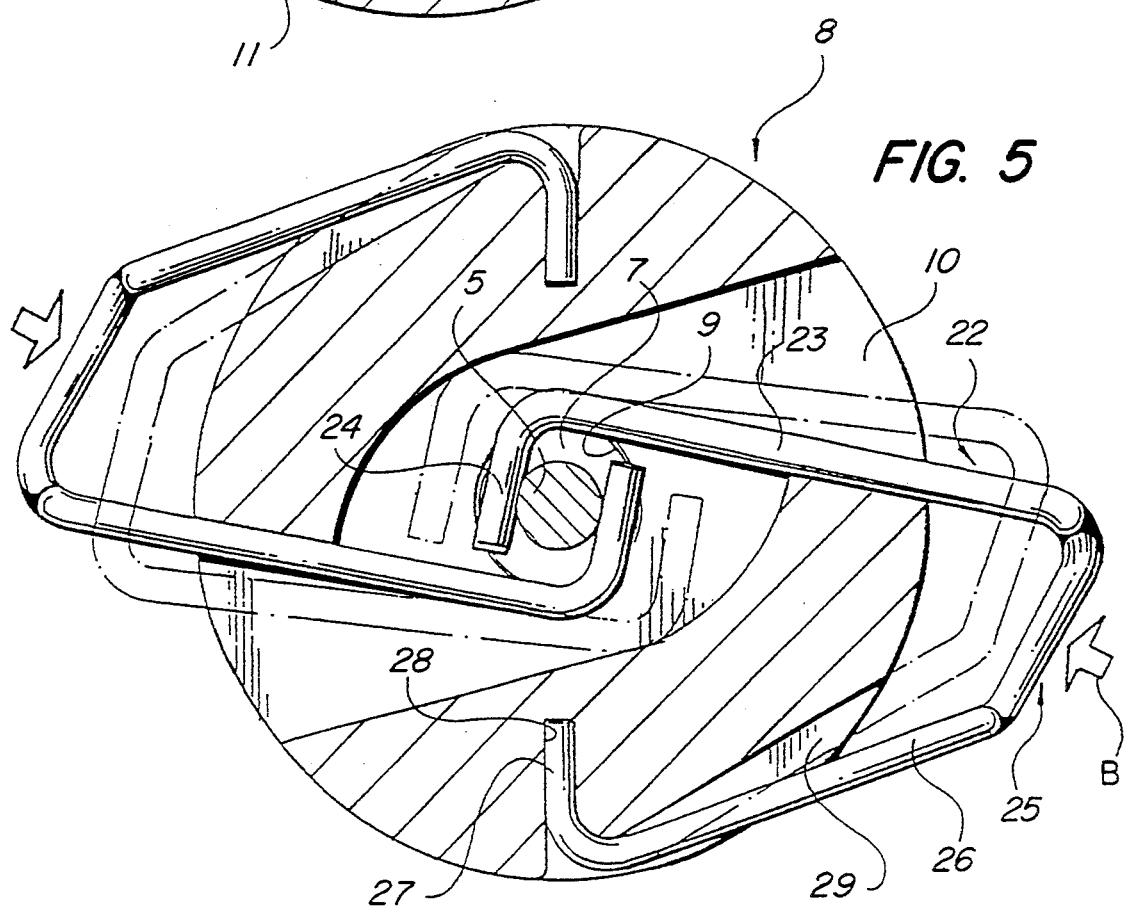
FIG. 5 a sectional view similar to FIG. 4 in a further preferred embodiment of a fixing member.

The embodiment of a fixing member 8 illustrated in FIG. 5 is of similar design to that of FIGS. 2 to 4. Corresponding parts, therefore, bear the same reference numerals.

In contrast with the embodiment of FIGS. 2 to 4, the fixing member 8 according to FIG. 5 comprises a continuous shaft 10, i.e., a widening 11 and a wedge 12 are not present.

The U-shaped detent element 16 is replaced by two detent elements 22 of identical design arranged diametrically opposite each other in the fixing member, only one of which will be described hereinbelow. The detent element is integrally formed from elastic spring wire and comprises a detent arm 23 which dips into the shaft with an inwardly bent end 24. The end 24 engages the insert opening 9 and can be pushed out of the insert opening by the detent arm 23 being displaced parallel to its longitudinal direction. The end of the detent arm 23 protruding outwards from the shaft is bent approximately at a right-angle and forms a pressure section 25 in which the spring wire is additionally bent perpendicularly out of the shaft plane in a similar way as in the pressure section 20 of the detent element 16 of the embodiment of FIGS. 2 to 4.

Adjoining this pressure section 25 is a spiral spring 26 which is inserted with a bent end 27 in a substantially radially extending bore 28 of the fixing member. The spiral spring section 26 engages partially a groove 29 in the fixing member open towards the circumference and is thereby guided upwardly and downwardly.

In the relaxed state, this detent element 22 stands in the position illustrated in continuous lines in FIG. 4 in which the bent end 24 of the detent arm 23 engages the insert opening 9. By pressing on the pressure section 25 in the direction of arrow B in FIG. 5, the detent arm 23 is pushed into the shaft 10 by elastic bending of the spiral spring 26 until it assumes the position illustrated in dot-and-dash lines in FIG. 5 in which the bent end 24 is removed from the insert opening 9.

Since two such detent elements 22 are provided in the fixing member according to FIG. 5, the bent ends 24 of these two detent elements lie at opposite ends of the extension 5 in its annular groove 7 when the fixing member is pushed onto the extension. To release it, both detent elements 22 have to be pressed in in the pressure section 25 for only when both ends 24 are disengaged from the insert opening 9 is removal of the fixing member possible.

With the fixing member of FIG. 5, the detent elements 22 are also easily inserted therein. It is sufficient to bend open the U-shaped detent element slightly and to introduce the detent arm into the shaft while simultaneously pressing the end 27 of the spiral spring 26 into the bore 28.

In the embodiment of a fixing member illustrated in FIGS. 6 and 7 which is of essentially the same design as that of FIG. 5 and in which like parts also bear the same reference numerals as in the fixing members described hereinabove, the fixing member itself is comprised of two halves 30, 31 which are separated from one another along a plane substantially at the top side of the shaft and parallel to the plane of the shaft. The shaft is thus arranged in the bottom half 31 and is open towards the separating plane. The same applies to the groove 29 formed in the bottom half as groove delimited on both sides and open towards the separating plane. This enables the spiral spring 26 to be inserted in the bore and the groove 28 and 29, respectively, from above, with the detent arm 23 being placed from above into the upwardly open shaft 10.

After insertion of the spiral springs 26 into the bottom half, the top half 30 closes the shaft 10 and the bore 28 as well as the groove 29 on the top side, the spiral springs 26 thereby being undetachably fixed in the fixing member. The precise alignment of the two halves 30 and 31 is implemented by pins 32 which are formed on the top half 30, thereby protruding from the underside thereof, and dip into corresponding bores 33 in the bottom half (FIG. 6).

The halves which are placed on one another in this way may consist of a plastic material which makes it possible for the two halves to be lastingly joined, for example, by ultrasonic welding.

I claim:

1. A screen basket for sterilizing containers comprising:

a bottom with openings therein;

at least one holding element fixed on said bottom and having an extension which extends through at least one opening of the bottom;

a releasable fixing member surrounding the extension on the underside of the bottom, said fixing member carrying a detent element and having contact surfaces formed by a wedge which is oriented towards an insert opening for the extension, said detent element being constructed and arranged to releasably engage a recess on a side surface of said extension by elastic deformation;

wherein:

said detent element comprises two parallel resilient detent arms, the mutual spacing of which is less than the outer diameter of the extension, and said two detent arms are mounted in the fixing member for displacement parallel to their longitudinal direction toward said wedge with free ends thereof constructed and arranged to be spread apart by said contact surfaces when displaced toward said wedge.

2. A screen basket as defined in claim 1, wherein said recess comprises a circumferential groove, and said detent element engages said groove on opposite sides of the extension.

3. A screen basket as defined in claim 1, wherein said extension includes a tip constructed and arranged to push the arms of said detent element elastically apart when the fixing member is pushed onto the extension.

4. A screen basket as defined in claim 1, wherein:
   said fixing member comprises a shaft extending transversely to said insert opening, said shaft being open at a side of said fixing member;
   said detent element protrudes laterally from the open shaft and is displaceable therein;
   the free ends of the detent arms are bent in order to engage a widening at the sides of said shaft within the fixing member when the detent arms are not deformed;
   said detent arms are joined together by a crosspiece at their end which protrudes from said shaft; and
   said shaft is wide enough to allow the detent arms to be elastically spread apart until their mutual spacing corresponds at least to the outer diameter of said extension.

5. A screen basket as defined in claim 4 wherein the bent free ends of said detent arms are short enough to fit completely within the interior of the shaft when the detent arms are bent together.

6. A screen basket as defined in claim 4 wherein the spacing between the detent arms is greater adjacent said crosspiece than in the interior of the fixing member adjacent said insert opening.

7. A screen basket as defined in claim 4 wherein said detent arms are bent perpendicularly at their end protruding from said open shaft near said crosspiece.

8. A screen basket as defined in claim 1 wherein said detent element comprises spring wire.

9. A screen basket for sterilizing containers comprising:
   a bottom with openings therein;
   at least one holding element fixed on said bottom and having an extension which extends through at least one opening of the bottom;
   a releasable fixing member on the underside of the bottom, said fixing member having an insert opening through which the extension passes and carrying a detent element constructed and arranged to releasably engage a recess on a side surface of said extension by elastic deformation;
   wherein:
      said detent element engages said recess with a bent end of a detent arm that overlaps a portion of said insert opening;
      said detent arm is resiliently mounted in the fixing member via an integrally formed spring wire between the detent arm and the fixing member, a portion of the detent arm emerging from the fixing member to enable displacement of said bent end transversely to said insert opening when the emerging portion is pushed; and
      said spring wire is mounted to said fixing member via a bent end portion thereof that engages a retaining recess in the fixing member.

10. A screen basket as defined in claim 9 wherein said fixing member comprises two halves in the plane of said detent arm, one of said halves having a groove facing the other half for accommodating a portion of said spring wire including the bent end portion thereof.

11. A screen basket as defined in claim 10 wherein said two halves are aligned relative to each other by pins and corresponding openings that engage the pins.

12. A screen basket as defined in claim 10 wherein said two halves are plastic and share an ultrasonically welded seam.

13. A screen basket as defined in claim 9 wherein said spring wire includes a pressure section extending transversely from the portion of said detent arm that emerges from said fixing member.

14. A screen basket as defined in claim 9 wherein two detent elements of identical design with bent ends are arranged diametrically opposite in said fixing member.

15. A screen basket as defined in claim 10 wherein two detent elements of identical design with bent ends are arranged diametrically opposite in said fixing member.

16. A screen basket as defined in claim 13 wherein two detent elements of identical design with bent ends are arranged diametrically opposite in said fixing member.

* * * * *

UNITED STATES PATENT AND TRADEMARK OFFICE
CERTIFICATE OF CORRECTION

PATENT NO. : 5,433,930
DATED : July 18, 1995
INVENTOR(S) : Taschner

It is certified that error appears in the above-identified patent and that said Letters Patent is hereby corrected as shown below:

On the title page, left column, immediately above "[51] Int. Cl.$^6$ ............... A61L 2/00; A61L 2/26" add:

-- [30] Foreign Application Priority Data Oct. 6, 1988 [DE] Fed. Rep. of Germany ............... P38 33 998.6 -- .

Signed and Sealed this

Seventeenth Day of October, 1995

Attest:

BRUCE LEHMAN

Attesting Officer

Commissioner of Patents and Trademarks